US011058441B2

(12) United States Patent
Grinnell, II

(10) Patent No.: US 11,058,441 B2
(45) Date of Patent: Jul. 13, 2021

(54) LASER ASSISTED SURGICAL RESECTION ALIGNMENT GUIDE

(71) Applicant: LASRlign, LLC, Waveland, MS (US)

(72) Inventor: Orton F. Grinnell, II, Waveland, MS (US)

(*) Notice: Subject to any disclaimer, the term of this patent is extended or adjusted under 35 U.S.C. 154(b) by 296 days.

(21) Appl. No.: 16/058,389

(22) Filed: Aug. 8, 2018

(65) Prior Publication Data
US 2020/0046379 A1 Feb. 13, 2020

(51) Int. Cl.
*A61B 17/17* (2006.01)
*A61B 17/00* (2006.01)

(52) U.S. Cl.
CPC ...... *A61B 17/1707* (2013.01); *A61B 17/1764* (2013.01); *A61B 2017/00734* (2013.01)

(58) Field of Classification Search
CPC .. A61B 17/15–158; A61B 17/16–1697; A61B 2017/1648; A61B 2017/1651; A61B 2017/1653; A61B 17/17–1796
See application file for complete search history.

(56) References Cited

U.S. PATENT DOCUMENTS

| | | | | |
|---|---|---|---|---|
| 2007/0043375 A1* | 2/2007 | Anissian | ............... | A61B 17/15 606/87 |
| 2009/0076507 A1* | 3/2009 | Claypool | ............... | A61B 90/06 606/53 |
| 2009/0234360 A1* | 9/2009 | Alexander | ............. | A61B 17/15 606/88 |
| 2011/0106092 A1* | 5/2011 | Fisher | .................... | A61B 90/13 606/88 |
| 2012/0184961 A1* | 7/2012 | Johannaber | .......... | A61B 17/157 606/88 |
| 2018/0214240 A1* | 8/2018 | Hwang | ............. | A61B 17/1717 |

* cited by examiner

*Primary Examiner* — Matthew J Lawson
(74) *Attorney, Agent, or Firm* — Emily L. Gordy; J. Matthew Miller, III; Carver, Darden, Koretzky, Tessier, Finn, Blossman & Areaux, LLC

(57) ABSTRACT

The present invention relates to a laser assisted surgical resection alignment guide for performing joint resection surgery. The present invention includes a base plate containing a switch which activates orthogonal laser assemblies when the laser assisted surgical resection alignment guide is inserted into a surgical block. The orthogonal laser assemblies each project beams which are each refracted by lenses to project two laser lines onto a human who has been prepared for surgery.

11 Claims, 12 Drawing Sheets

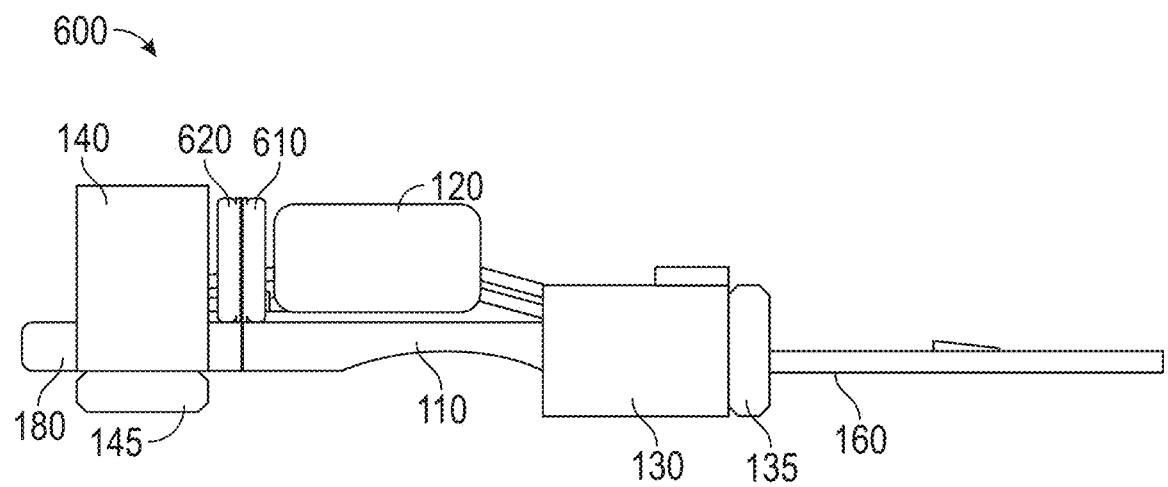
FIG. 6B
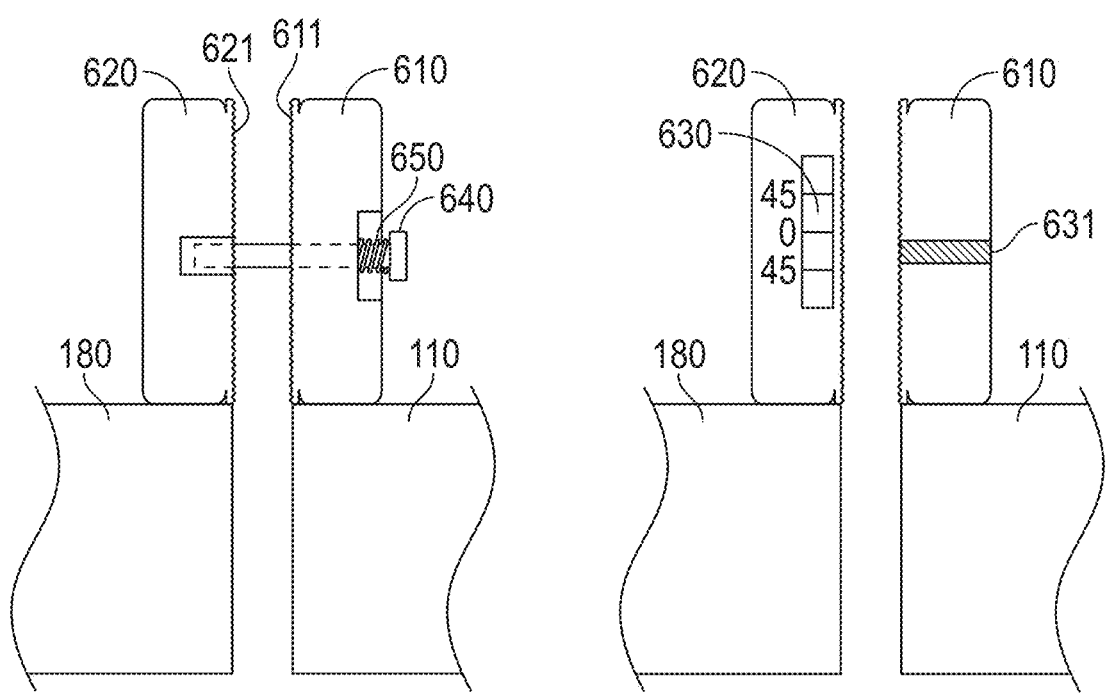
FIG. 6C
FIG. 6D

LASER ASSISTED SURGICAL RESECTION ALIGNMENT GUIDE

BACKGROUND OF THE INVENTION

I. Field of the Invention

The present invention relates generally to an alignment guide for use in total joint replacement orthopedic surgery, which uses lasers to project lines to guide cutting.

II. General Background

Current technology uses computer aided guidance or MRI generated cutting angles. I speculate that such techniques are not completely accurate when used in real world scenarios. Moreover, even with computer aided guidance and MRI generated cutting angles, most surgeons verify the straightness and alignment of their cuts (e.g., cutting, or resecting, a joint in a total joint replacement surgery) using metal rods and manual guides before committing to their cuts.

In view of the foregoing, there is, in our view, a continuing need for an improved guide for assisting surgeons in performing accurate surgical resections.

SUMMARY OF THE INVENTION

In accordance with an embodiment, the present invention is a laser guide, comprising a base plate, an end plate, a horizontal laser assembly, a vertical laser assembly, a switch, and a battery; wherein said horizontal laser assembly and said vertical laser assembly both comprise a laser emitting device and a lens, said lens being affixed to a light emitting end of said laser emitting device; wherein said horizontal laser assembly is affixed to said base plate, parallel to said base plate, and said vertical laser assembly is affixed to said end plate, orthogonal to said end plate; wherein said switch and said battery are affixed to said base plate and said switch, said horizontal laser assembly and said vertical laser assembly are electrically connected to said battery; and wherein said end plate is rotationally connected to said base.

In accordance with another embodiment, the present invention is a method of verifying a position of a surgical cut, comprising the steps of: inserting a laser guide into a surgical block mounted on a knee of a human for performing a knee surgery; enabling said laser guide to project horizontal laser light and vertical laser light onto said human; using said horizontal laser light to verify a position of said surgical cut; and using said vertical laser light to verify alignment of said surgical cut; wherein said laser guide comprises a base plate, an end plate, a horizontal laser assembly, a vertical laser assembly, a switch, and a battery; wherein said horizontal laser assembly and said vertical laser assembly both comprise a laser emitting device and a lens, said lens being affixed to a light emitting end of said laser emitting device; wherein said horizontal laser assembly is affixed to said base plate, parallel to said base plate, and said vertical laser assembly is affixed to said end plate, orthogonal to said end plate; wherein said switch and said battery are affixed to said base plate and said switch, said horizontal laser assembly and said vertical laser assembly are electrically connected to said battery; and wherein said end plate is rotationally connected to said base plate.

BRIEF DESCRIPTION OF THE DRAWINGS

The foregoing and other objects, features, and advantages of the invention are apparent from the following detailed description taken in conjunction with the accompanying drawings in which like parts are given like reference numerals and, wherein:

FIG. 6B depicts a side view of an alternate embodiment of a laser guide.

FIG. 6C depicts a side cross section view of a portion of an alternate embodiment of a laser guide.

FIG. 6D depicts a side view of a portion of an alternate embodiment of a laser guide.

DETAILED DESCRIPTION

The disclosed invention is a laser assisted surgical resection alignment guide (referred to herein as a laser guide), and a method of using a laser guide to perform surgery.

Figure 1A:
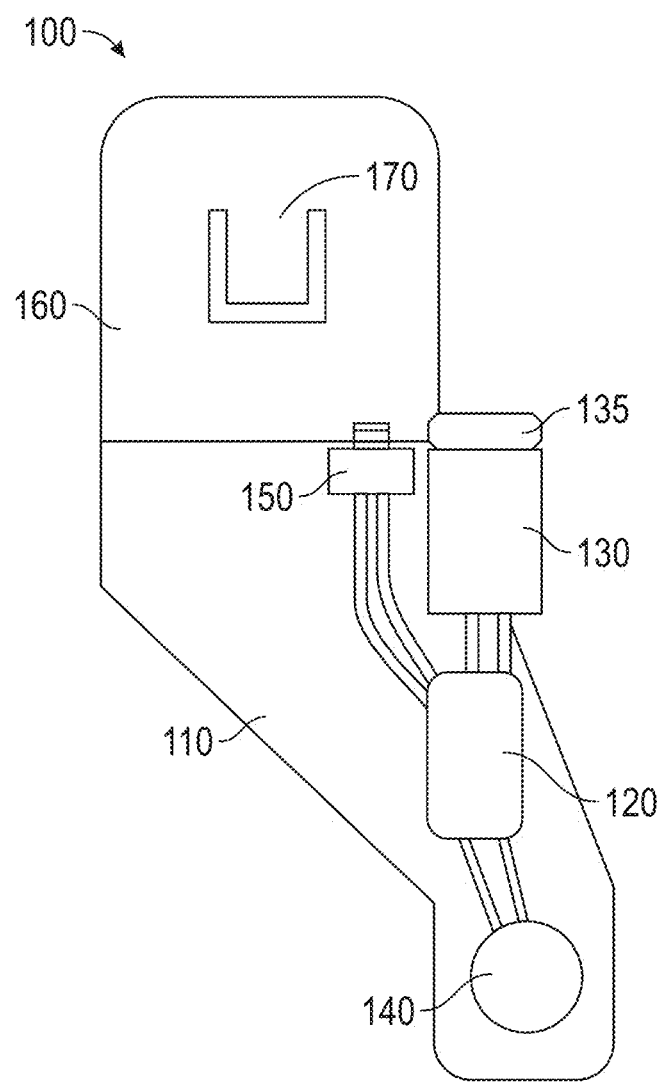
FIG. 1A depicts a top view of one embodiment of a laser guide.
Figure 1B:
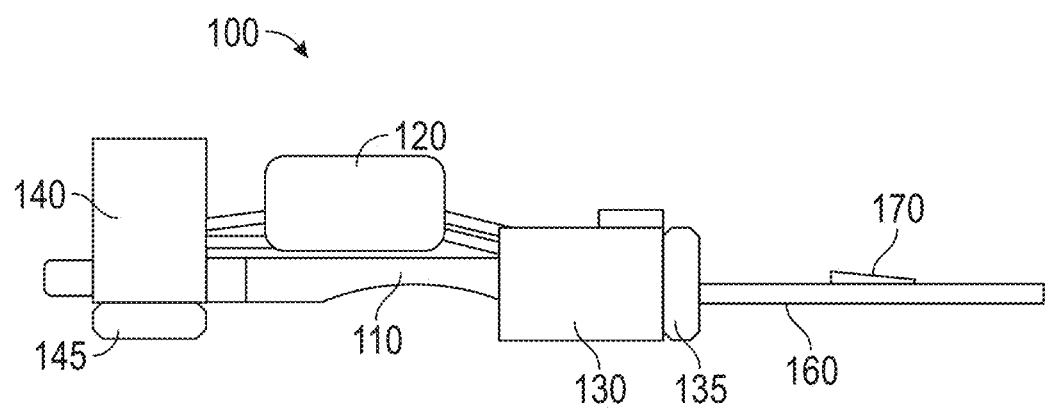
FIG. 1B depicts a side view of one embodiment of a laser guide.

FIGS. 1A and 1B depict a top view and a side view of an embodiment of laser guide 100. Laser guide 100 comprises base plate 110, battery 120, horizontal laser 130, horizontal laser lens 135, vertical laser 140, vertical laser lens 145, switch 150, insertion plate 160, and tab 170. Horizontal laser 130, vertical laser 140, battery 120, and switch 150 are each affixed to base plate 110. Horizontal laser 130, vertical laser 140, battery 120, and switch 150 may be affixed to base plate 110 by any suitable means. Horizontal laser 130, vertical laser 140, and switch 150 are each electrically connected to battery 120. In an embodiment, such electrical connections are made by copper wires, but any suitable electrical connector may be used. Horizontal laser lens 135 is affixed to, and optically coupled with, horizontal laser 130. Vertical laser lens 145 is affixed to, and optically coupled with, vertical laser 140. Insertion plate 160 is connected to base plate 110.

Base plate 110 provides an offset seat for affixing horizontal laser 130 and vertical laser 140, such that horizontal laser 130 and vertical laser 140 are offset from insertion plate 160. FIG. 1 depicts such an offset seat to the right of insertion plate 160. In other embodiments, vertical laser 140 is offset to the left of insertion plate 160.

In an embodiment, base plate 110 is formed from stainless steel and is approximately 3 mm thick.

Battery 120 is any suitable battery capable of powering horizontal laser 130 and vertical laser 140. In one embodiment, battery 120 is a 1.5 v battery pack.

Horizontal laser 130 and vertical laser 140 are each laser emitting devices capable of emitting a straight beam of laser light of sufficient strength that the light is both visible when diffracted as discussed herein and not so powerful as to harm a human when used in surgery. Horizontal laser lens 135 is affixed to horizontal laser 130 such that light emitted from horizontal laser 130 passes through, and is refracted by, horizontal laser lens 135. Together, horizontal laser 130 and horizontal laser lens 135 are a horizontal laser assembly. Vertical laser lens 145 is affixed to vertical laser 140 such that light emitted from vertical laser 140 passes through, and is refracted by, vertical laser lens 145. Together, vertical laser 140 and vertical laser lens 145 are a vertical laser assembly.

In one embodiment, horizontal laser 130 and vertical laser 140 are 5 milliwatt laser devices emitting laser light at a frequency of 532 nanometers. However, I speculate that laser devices of different power (including, without limitation, between 5 and 10 milliwatts) and emitting different frequencies of visible light may be used, so long as the light is visible and does not harm a human when used in surgery.

Horizontal laser 130 projects a laser beam parallel to base plate 110, and vertical laser 140 projects a laser beam perpendicular to base plate 110. Thus, the beams projected by horizontal laser 130 and vertical laser 140 are orthogonal.

Horizontal laser lens 135 and vertical laser lens 145 are lenses which refract a straight laser beam, such that the laser beam spreads from a straight line triangularly into a plane, such that the laser beam, if projected onto a flat surface, will create an illuminated line on such flat surface. However, in certain embodiments, one or more of the laser beams are projected onto irregular surfaces (e.g., bone), so that the projection does not create a straight line, but rather, helps a surgeon visualize a plane into which a cut will be made. In one embodiment, horizontal laser lens 135 and vertical laser lens 145 are lenses obtained from a laser level. I speculate that any suitable cylindrical lens, Powell lens, or fan angle generator lens may be used, so long as the light emitted sufficiently illuminates the surgical site.

Switch 150 is switch that is activated when laser guide 100 is inserted into a surgical block. In one embodiment, switch 150 is a pressure switch. In other embodiments, switch 150 is activated (i.e., forms a closed circuit and turns laser guide 100 on) upon electrical contact with a surgical block.

Insertion plate 160 a member affixed to, and extending in the same plane as, base plate 110. Insertion plate 160 serves to hold laser guide 100 in place when in use. Thus, the length and width of insertion plate 160 are sufficient to hold the weight of the other portions of laser guide 100.

In an embodiment, insertion plate 160 is 1 mm thick and 30 mm wide.

In an embodiment, base plate 110 and insertion plate 160 are formed from a single piece of material. In some embodiments, that material is stainless steel.

Tab 170 is a portion of insertion plate 160 which is raised above other portions of insertion plate 160 to create a flexible tab which depresses and creates fiction between tab 170 and a surgical block when insertion plate 160 of laser guide 100 is inserted into said surgical block.

In one embodiment, tab 170 is formed by a void in insertion plate 160 creating a rectangularly shaped raised tab. However, other geometries of tab 170 will work, so long as tab 170 creates sufficient friction to allow insertion plate 160 to anchor in a surgical block.

Figure 2A:
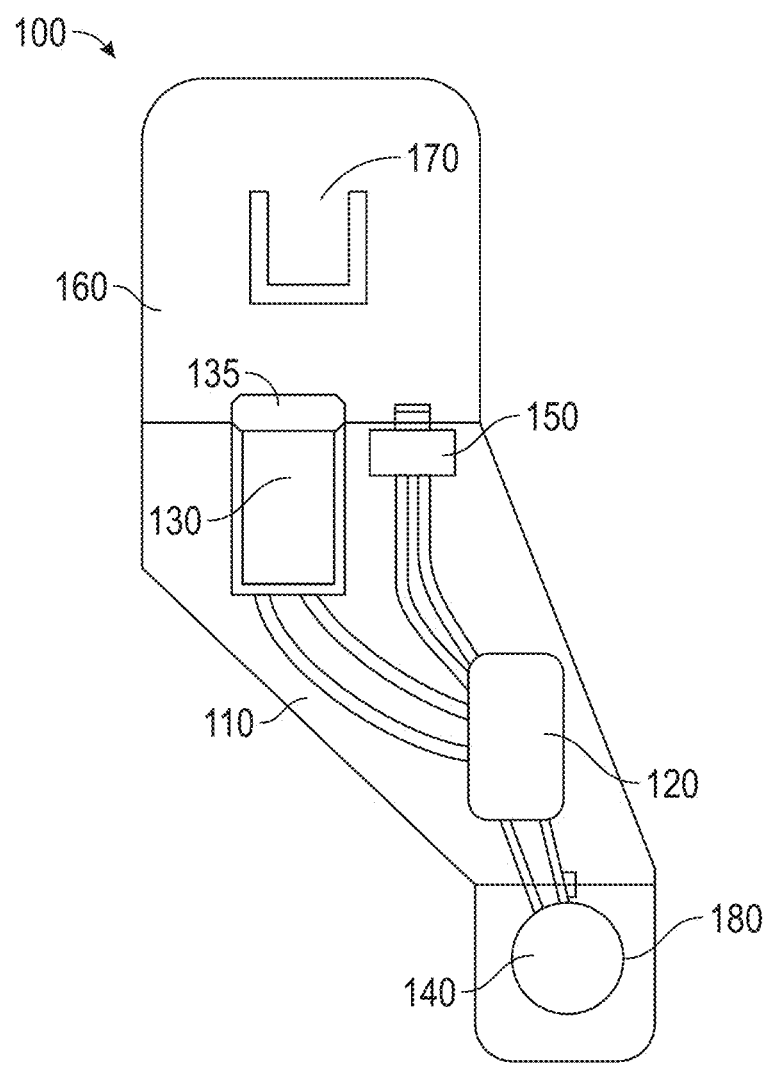
FIG. 2A depicts a top view of an alternate embodiment of a laser guide.
Figure 2B:
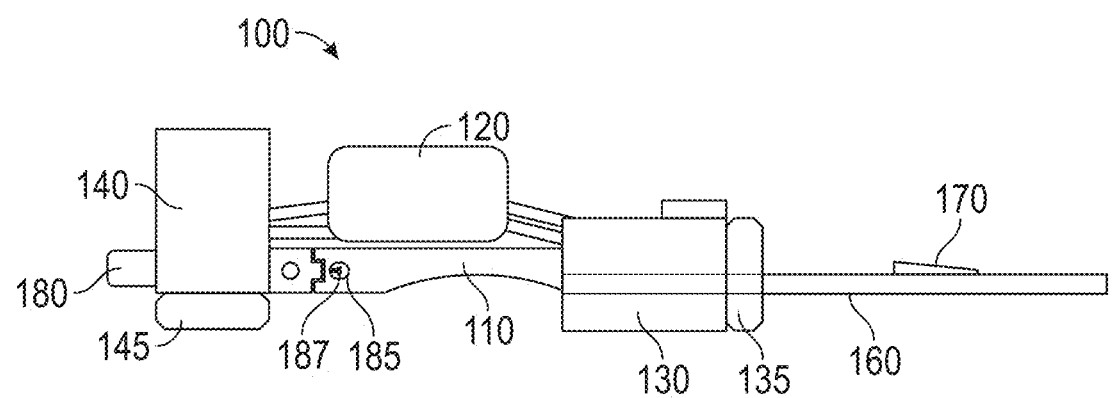
FIG. 2B depicts a side view of an alternate embodiment of a laser guide.
Figure 2C:
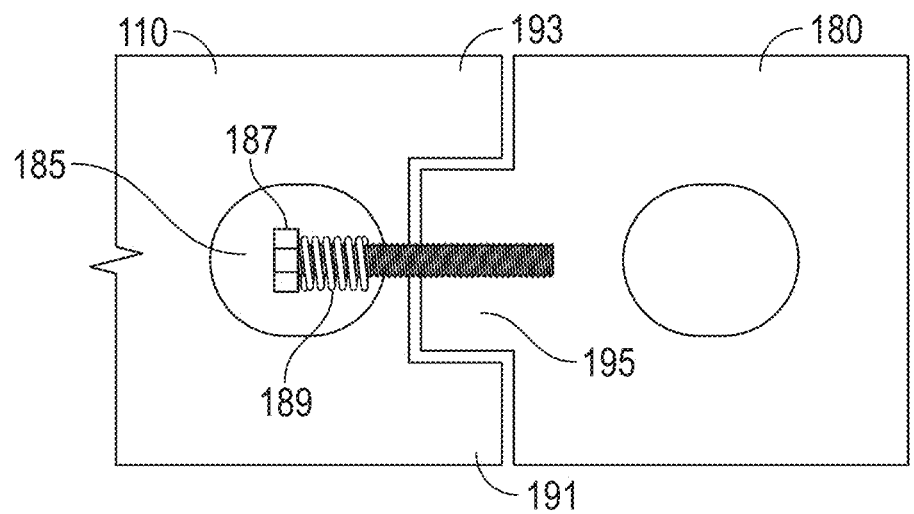
FIG. 2C depicts a side cross section view of a portion of an alternate embodiment of a laser guide.

FIGS. 2A, 2B, and 2C depict top, side, and side cross section views of an alternate embodiment of laser guide 100. This alternate embodiment of laser guide 100 is the same as discussed above, except that horizontal laser 130 and horizontal laser lens 135 are centrally located on base plate 110, and vertical laser 140 is attached to end plate 180, with end plate 180 rotationally and lockably connected to base plate 110.

FIG. 2C depicts the rotational locking connection between end plate 180 and base plate 110, depicting base plate 110, end plate 180, hole 185, pin 187, spring 189, bottom groove wall 191, top groove wall 193 (bottom groove wall 191 and top groove wall 193 forming a groove 194), and tongue 195. Pin 187 is headed and threaded, is affixed to tongue 195, and is inserted through spring 189.

Tongue 195 slides in and out of said groove 194. When no external force is applied to end plate 180, pressure of spring 189 pulls tongue 195 into said groove 194. In this state, end plate 180 is rotationally locked in place relative to base plate 110. When an external force is applied that opposes the force of spring 189, tongue 195 may be removed from said groove 194. When tongue 195 is removed of said groove 194, end plate 180 can rotate about pin 187. In such a fashion, the direction of vertical laser 140 can be changed to an opposite direction, allowing laser guide 100 to be used in surgeries for opposite sides of the body (as non-limiting examples, a left knee or a right knee).

Figure 2D:
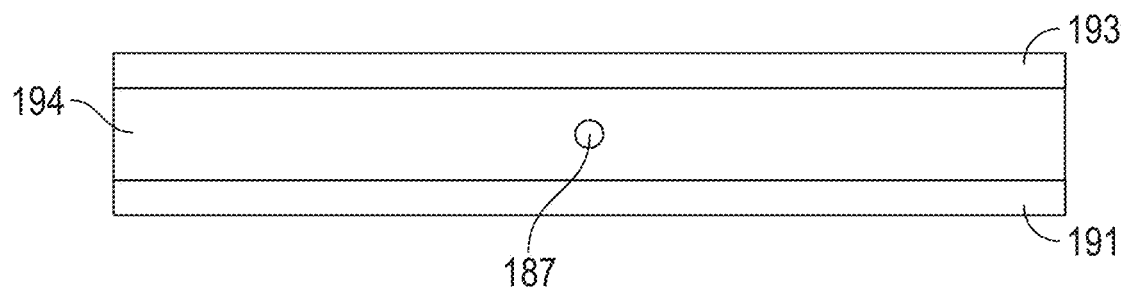
FIG. 2D depicts an end view of an embodiment of a base plate.

FIG. 2D depicts an end view of the embodiment of base plate 110 depicted in FIG. 2C, further depicting bottom groove wall 191, top groove wall 193, and groove 194.

Figure 2E:
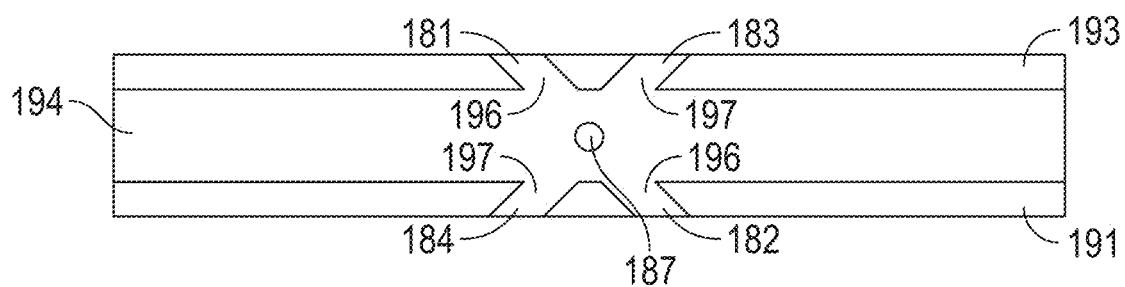
FIG. 2E depicts an end view of an alternate embodiment of a base plate.

FIG. 2E depicts an alternate embodiment of base plate 110 and differs from the base plate of FIG. 2D by further comprising first cutout 181, second cutout 182, third cutout 183, fourth cutout 184, first angled groove 196, and second angled groove 197. First cutout 181 and third cutout 183 are aligned to form first angled groove 196, and second cutout 182 and fourth cutout 184 are aligned to form second angled groove 197. In this embodiment, first angled groove 196 and second angled groove 197 each form 45 degree angles, respectively, with groove 194. Thus, in this embodiment, end plate 180 can be rotationally locked in place relative to base plate 110 through insertion into groove 194, first angled groove 196, or second angled groove 197 to achieve rotations relative to base plate 110 of 0 degrees (insertion into groove 194), 45 degrees (insertion into first angled groove 196), 135 degrees (insertion into second angled groove 197), 180 degrees (insertion inverted into groove 194), 225 degrees (insertion inverted into first angled groove 196), or 315 degrees (insertion inverted into second angled groove 197). The rotational alignments allowed by first angled groove 196 and second angled groove 197 allow for laser guide 100 to be used in additional types of surgeries (e.g., shoulder surgeries).

Figure 3:
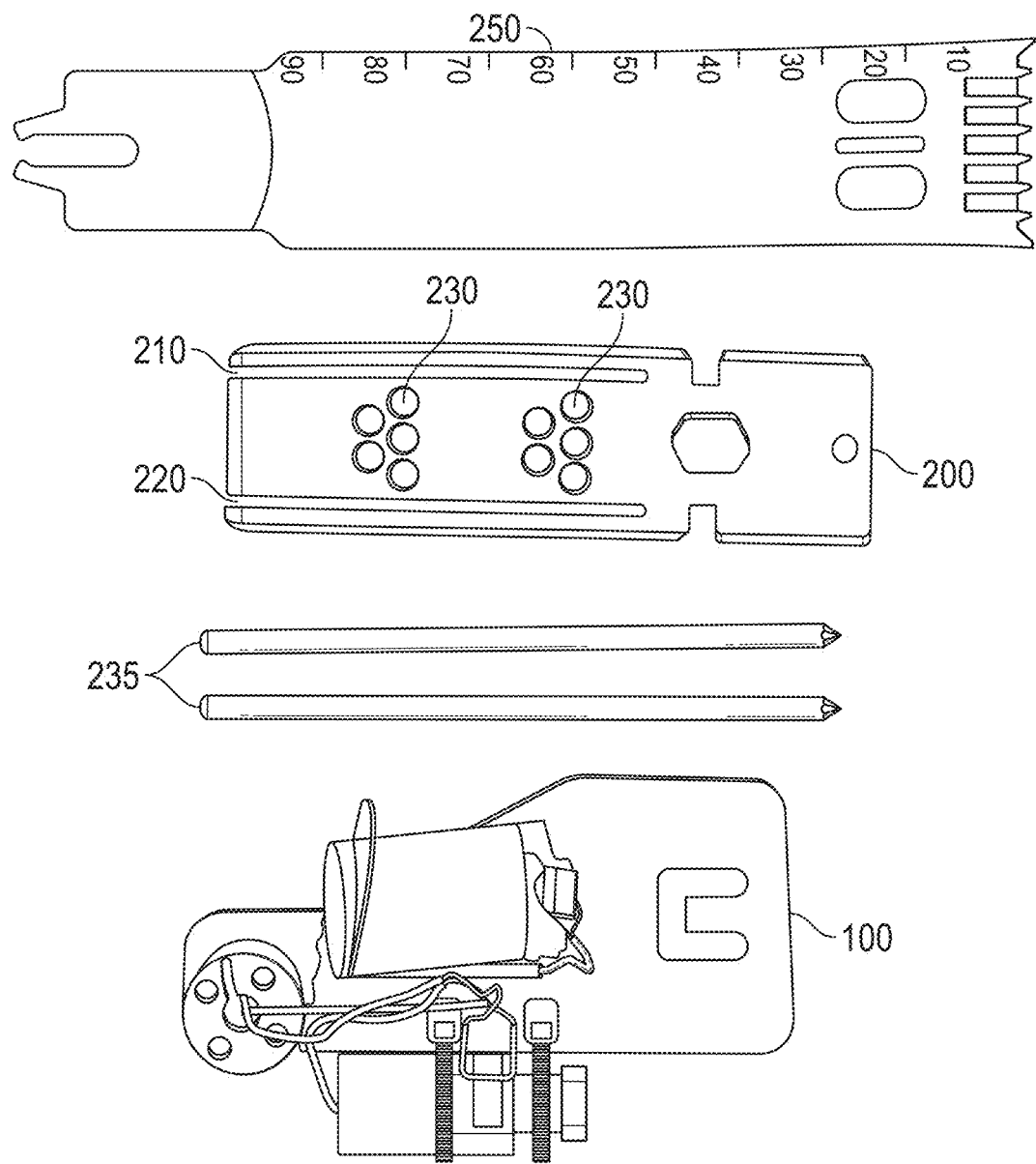
FIG. 3 depicts a top view of an embodiment of a laser guide, an embodiment of a surgical block, an embodiment of a resection saw, and an embodiment of guide rods.

FIG. 3 depicts a top view of a laser guide 100, a surgical block 200, a plurality of pins 235, and a resection saw 250. Surgical block 200 further comprises top slit 210, bottom slit 220, and a plurality of holes 230.

Top slit 210 and bottom slit 220 are each approximately 1.35 millimeters high. Thus, insertion plate 160 of laser guide 1100 may be inserted into either top slit 210 or bottom slit 220.

When in use, the plurality of pins 235 can be inserted through the plurality of holes 230 into holes drilled into bone. As such, the plurality of pins 235 limit the range of motion of surgical block 200 relative to bone.

Resection saw 250 can be used to cut bone. The position of surgical block 200 sets the location where resection saw 250 will cut bone.

Figure 4:
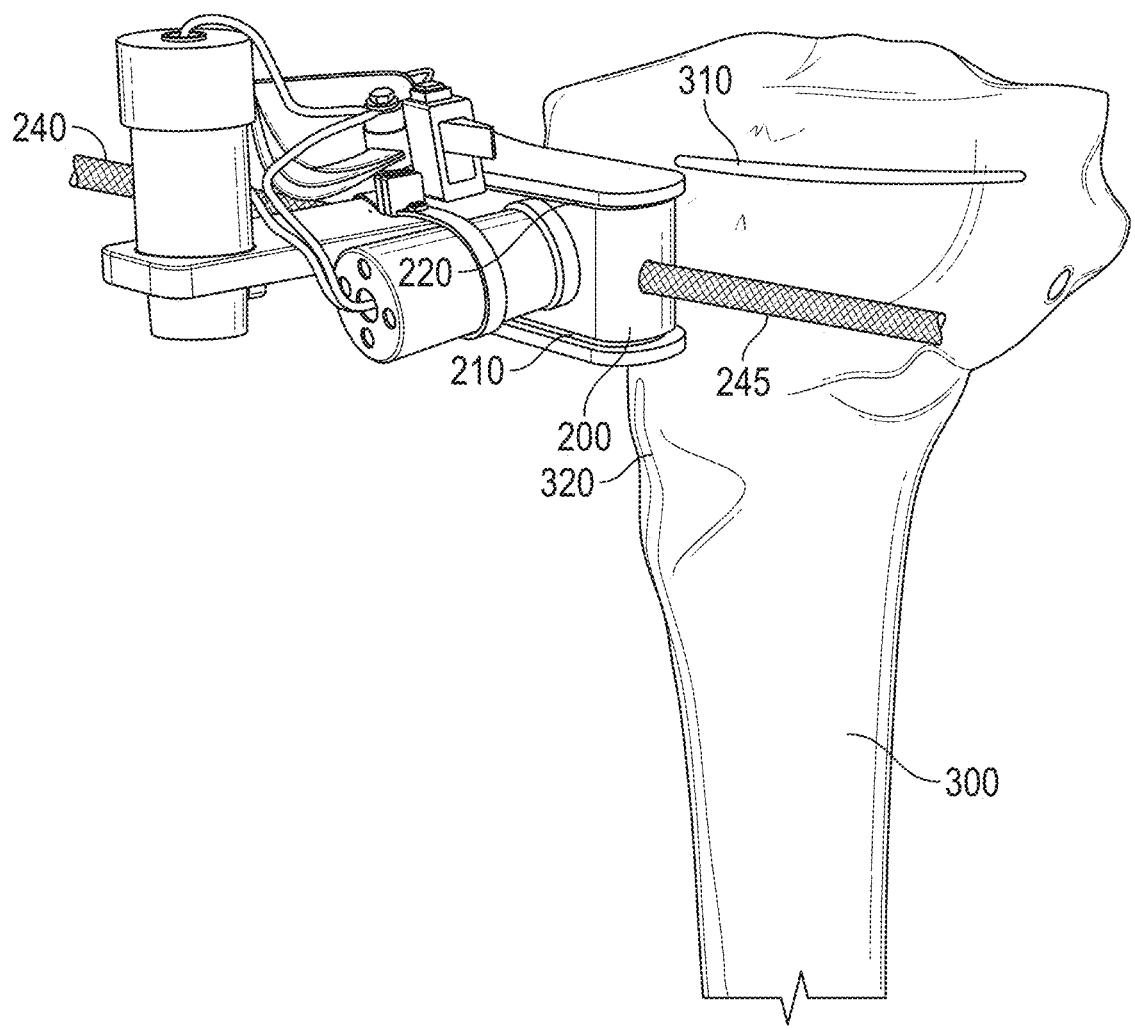
FIG. 4 depicts a rear view of an embodiment of a laser guide inserted into a surgical block with laser lines emitting from said laser guide onto bone.

FIG. 4 depicts laser guide 100 inserted into top slit 210 of surgical block 200. In this view, left gripping rod 240 and right gripping rod 245 are installed into surgical block 200.

Left gripping rod 240 and right gripping rod 245 are each metal rods with a cross-hatch texture for gripping during surgery and are used to maintain the position of surgical block 200 relative to bone.

FIG. 4 also depicts horizontal laser line 310 and vertical laser line 320 being emitted from laser guide 100 when laser guide 100 is activated by being inserted into surgical block 200. Horizontal laser line 310 provides a visible guide for performing a joint resection and shows a surgeon the location where resection saw 250 will cut through bone. In the embodiment depicted in FIG. 4, horizontal laser line 310 shows the resection level on the posterior slope of the tibia. In this type of surgery, end plate 180 is affixed at either 0 degrees or 180 degrees respective to base plate 110. Vertical laser line 320 provides a visible guide for performing a joint resection and shows a surgeon the line that is perpendicular to the surgeon's proposed cut, assisting the surgeon in identifying varus or valgus alignment.

Figure 5:
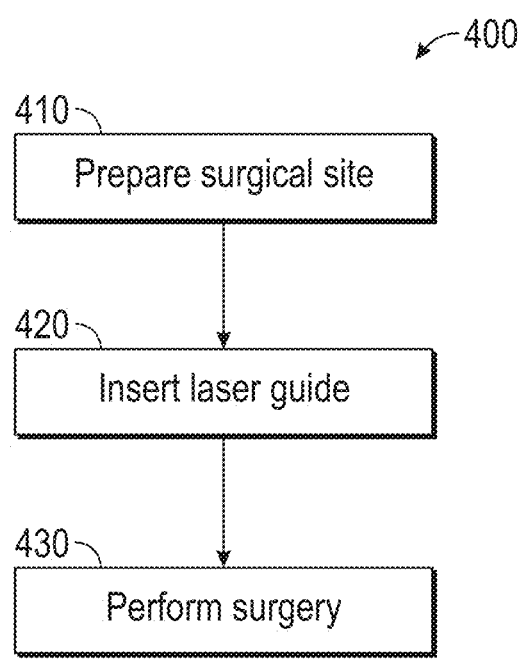
FIG. 5 depicts a method of using an embodiment of a laser guide to perform surgery.

FIG. 5 depicts laser guided surgical method 400 and comprises preparing step 410, insertion step 420, and surgical step 430.

In preparing step 410, the surgical site is prepared according to standard orthopedic steps, including the assembly and placement of surgical block 200. Laser guided surgical method 400 then proceeds to insertion step 420.

In insertion step 420, laser guide 100 is inserted into surgical block 200 and horizontal laser 130 and vertical laser 140 both illuminate and cast horizontal laser line 310 and vertical laser line 320, respectively. In insertion step 420, a surgeon uses the location of horizontal laser line 310 and vertical laser line 320, as cast onto bone, to verify the location of proposed cuts. In view of horizontal laser line 310 and vertical laser line 320, a surgeon may choose to reposition surgical block 200. Laser guided surgical method 400 then proceeds to surgical step 430. In some embodiments, laser guide 100 may be adjusted to alter the direction of, for example, vertical laser line 320, depending on the type of surgery to be performed and the location of the surgery on the patient. Thus, in some embodiments, the same laser guide 100 may be used for either left knee or right knee surgery.

In surgical step 430, laser guide 100 is removed, and a surgeon performs the desired surgery. Surgical step 430 and laser guided surgical method 400 are both concluded according to standard surgical techniques.

Figure 6A:
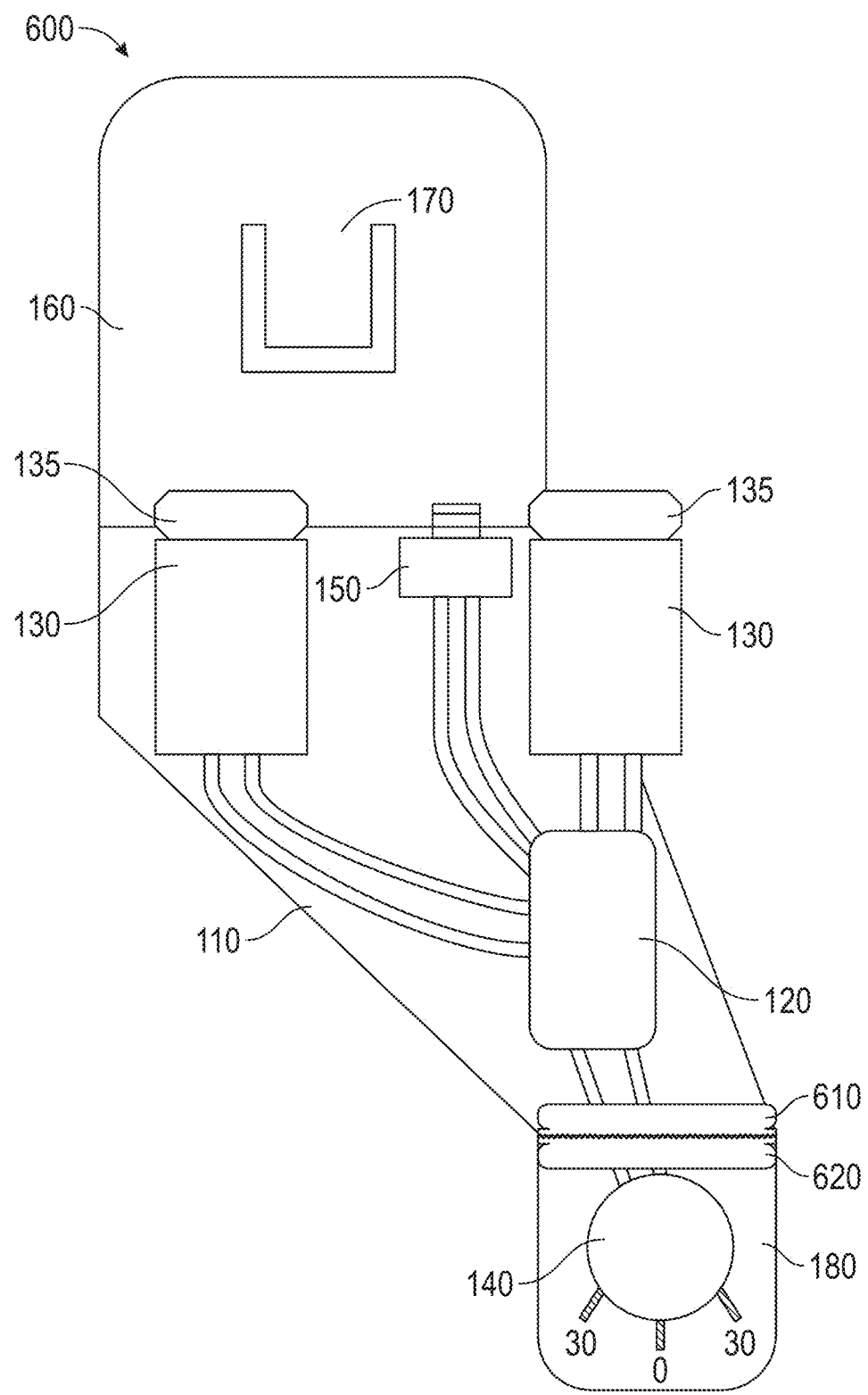
FIG. 6A depicts a top view of an alternate embodiment of a laser guide.

FIGS. 6A, 6B, and 6C depict top, side, and side cross section views of an alternate embodiment of a laser guide, referred to herein as an adjustable laser guide 600. Adjustable laser guide 600 is created and used in the same way as laser guide 100, except as discussed below. Adjustable laser guide 600 contains two horizontal lasers 130, both affixed to base plate 110, each with a horizontal laser lens 135. The two horizontal lasers 130 are parallel and the horizontal lasers 130 and horizontal laser lenses 135 are configured to emit light in the same plane such that the laser light from said horizontal lasers 130 projects onto a surface as a single straight line. Vertical laser 140 is attached to end plate 180, with end plate 180 rotationally coupled to base plate 110 by first connector plate 610 (affixed to base plate 110) and second connector plate 620 (affixed to end plate 180).

Additionally, in adjustable laser guide 600, vertical laser 140 is rotatable relative to end plate 180. Adjustable laser guide 600 further comprises left rotation degree display 660, right rotation degree display 662, and zero rotation degree display 665 (depicted in FIG. 6F), which provide a visual indicator of the amount of rotation of vertical laser 140 relative to end plate 180.

FIG. 6C depicts the rotational coupling between end plate 180 and base plate 110, depicting base plate 110, end plate 180, pin 640, and spring 650. Pin 640 is headed and threaded, is affixed to second connector plate 620, and is inserted through spring 650. As installed, spring 650 exerts a force on pin 640 and first connector plate 610, thereby causing first connector plate 610 and second connector plate 620 to be pressed together. First connector plate 610 further comprises first grooves 611, and second connector plate 620 further comprises second grooves 621. When first connector plate 610 and second connector plate 620 are pressed together, first grooves 611 come into contact with second grooves 621, resisting rotation of first connector plate 610 relative to second connector plate 620 about the axis of pin 640. However, with sufficient rotational force, spring 650 will compress, allowing first connector plate 610 to rotate relative to second connector plate 620.

FIG. 6D depicts horizontal rotation degree display 630 and horizontal rotation indicator 630. As first connector plate 610 rotates relative to second connector plate 620, horizontal rotation indicator 630 indicates a position on horizontal rotation degree display 630, allowing the user of the adjustable laser guide 600 to determine the amount of rotation between end plate 180 and base plate 110. In one embodiment, horizontal rotation degree display 630 has displays for −45, 0, and 45 degree rotations.

Figure 6E:
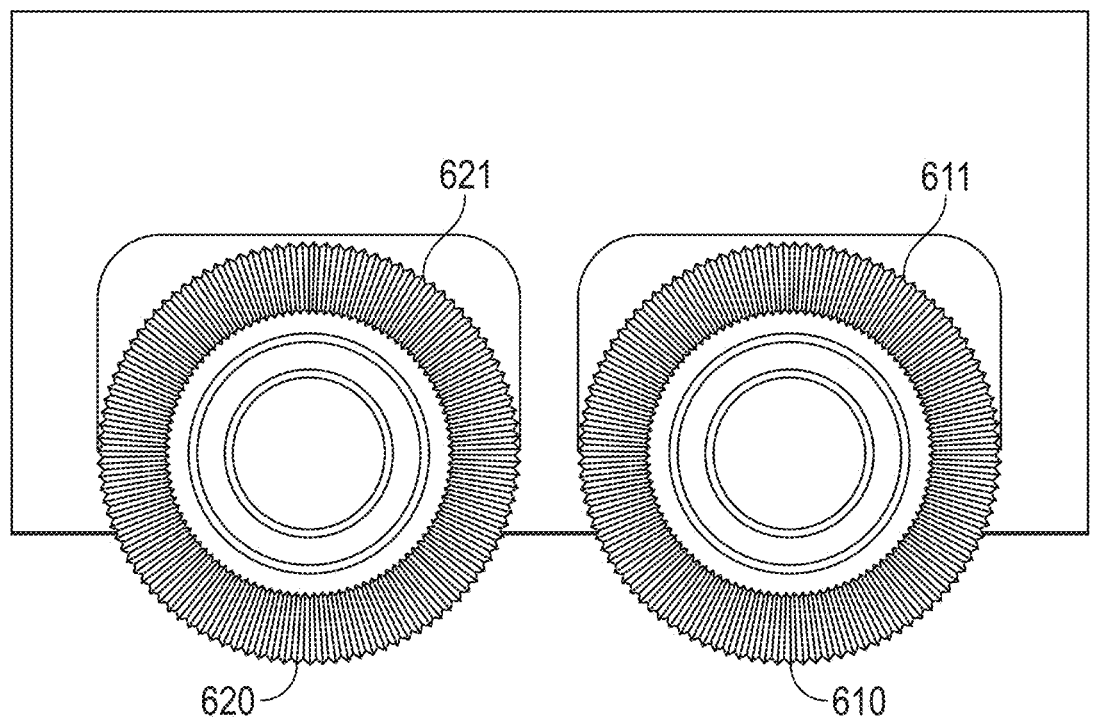
FIG. 6E depicts end views of an embodiment of rotation limiting connector plates.
Figure 6F:
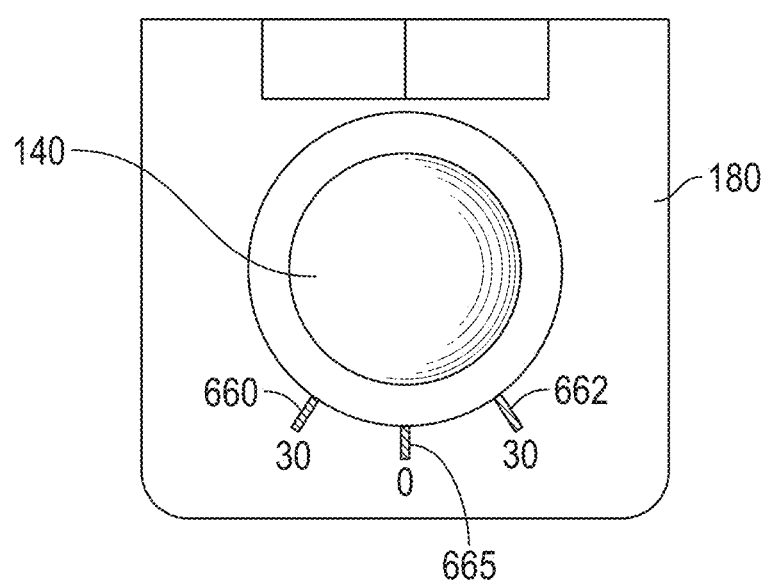
FIG. 6F depicts an embodiment of a rotation guide.

FIG. 6E is a detailed view of first connector plate 610 and second connector plate 620, showing first grooves 611 and second grooves 621, respectively FIG. 6F is a detailed view of left rotation degree display 660, right rotation degree display 662, and zero rotation degree display 665 on end plate 180 of adjustable laser guide 600. A rotation indicator is marked on vertical laser 140 (not depicted). Vertical laser 140 rotates relative to end plate 180 upon an axis orthogonal to end plate 180. As such rotation occurs, the rotation indicator of vertical laser 140 indicates an amount of rotation relative to left rotation degree display 660, right rotation degree display 662, and zero rotation degree display 665, allowing the user of the adjustable laser guide 600 to determine the amount of rotation of vertical laser 140 relative to end plate 180. In one embodiment, left rotation degree display 660 is marked at −30 degrees, right rotation degree display 662 is marked at 30 degrees, and zero rotation degree display 665 is marked at zero degrees.

Figure 7:
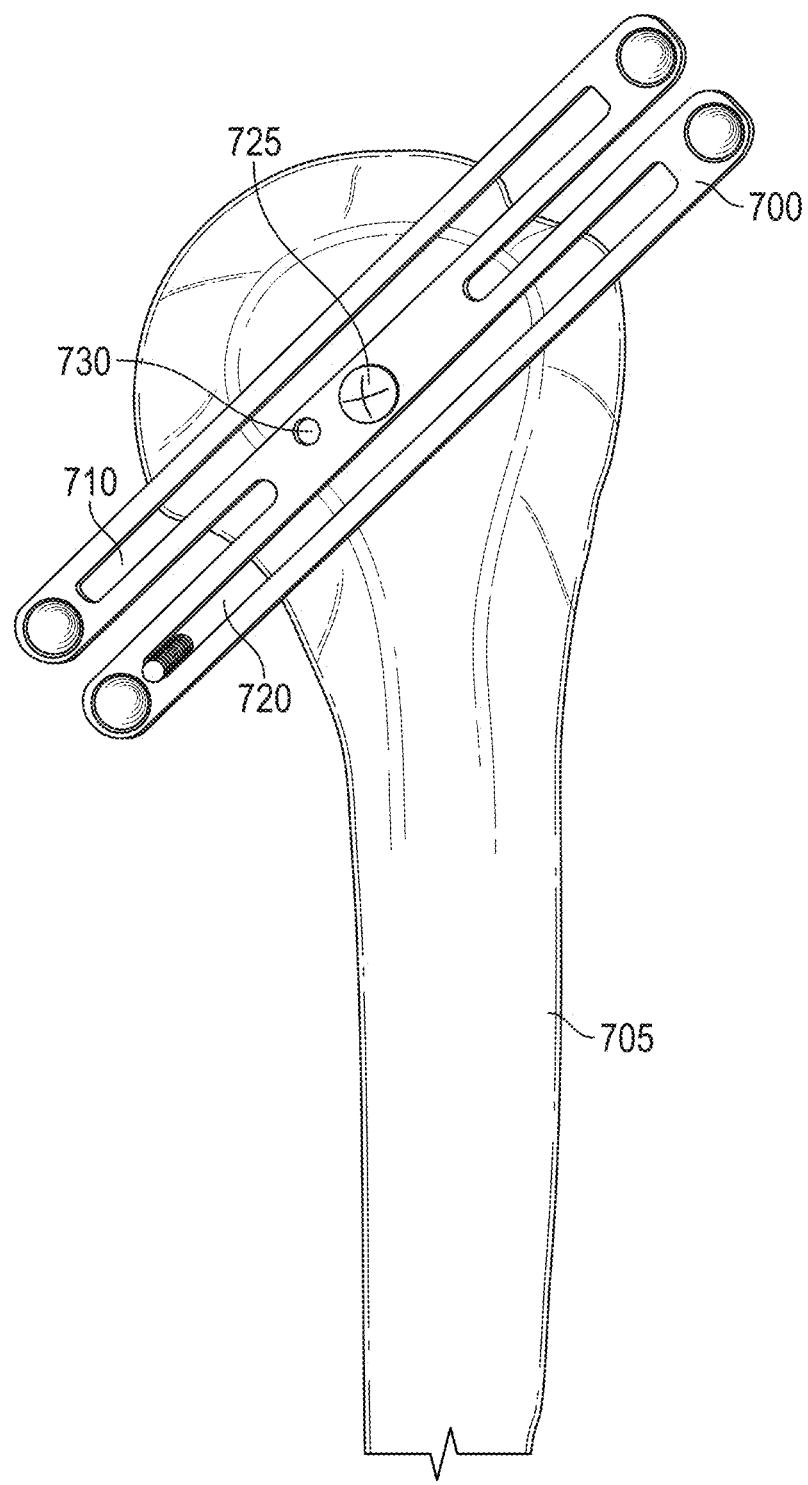
FIG. 7 depicts an embodiment of a surgical block affixed to a humerus bone.

FIG. 7 depicts a humerus bone 705 with surgical block 700 affixed thereto by screw 725. Surgical block 700 further comprises top slit 710, bottom slit 720, and hole 730.

Figure 8:
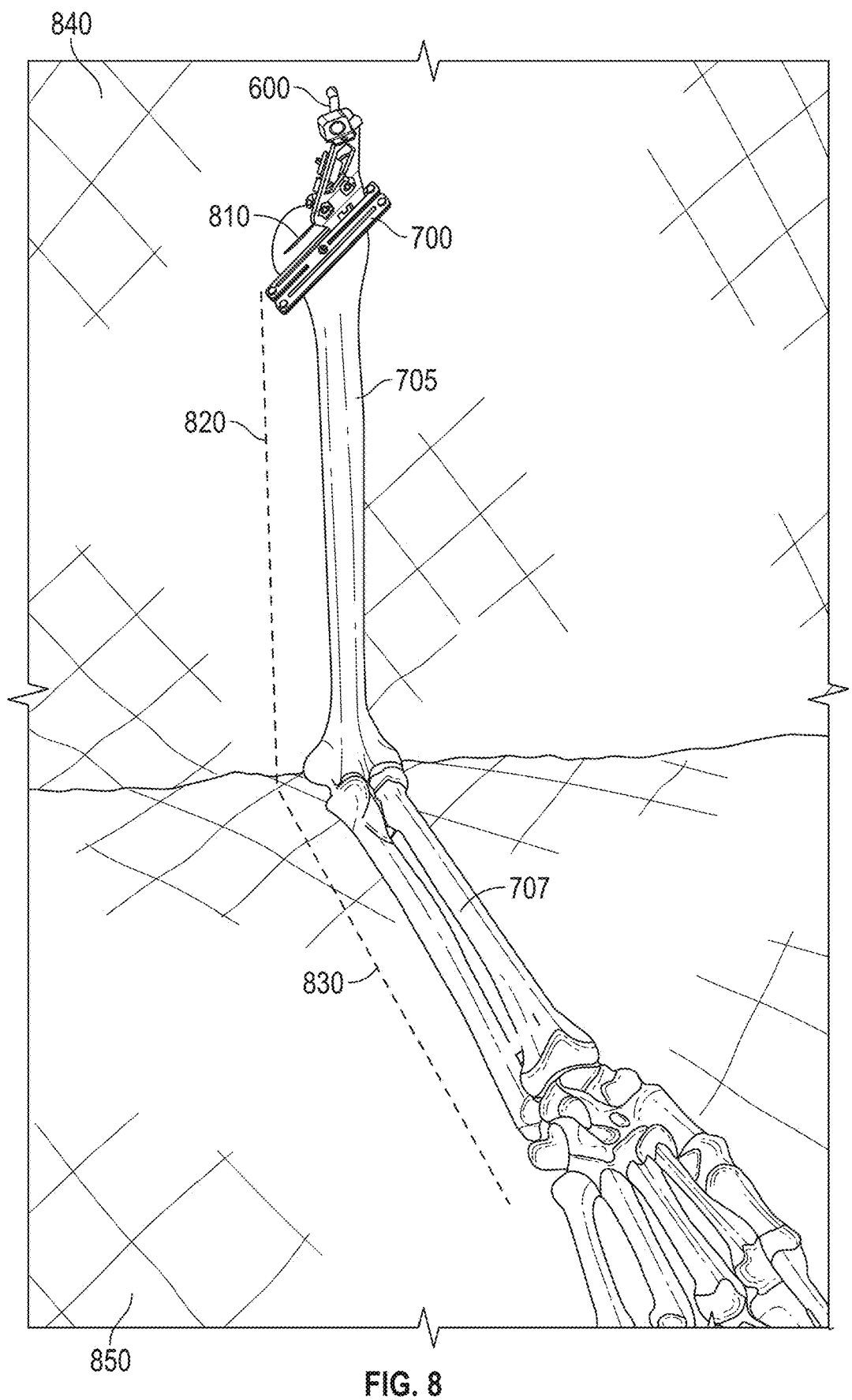
FIG. 8 depicts a front view of an alternate embodiment of a laser guide inserted into a surgical block with laser lines emitting from said alternate embodiment.
Figure 9:
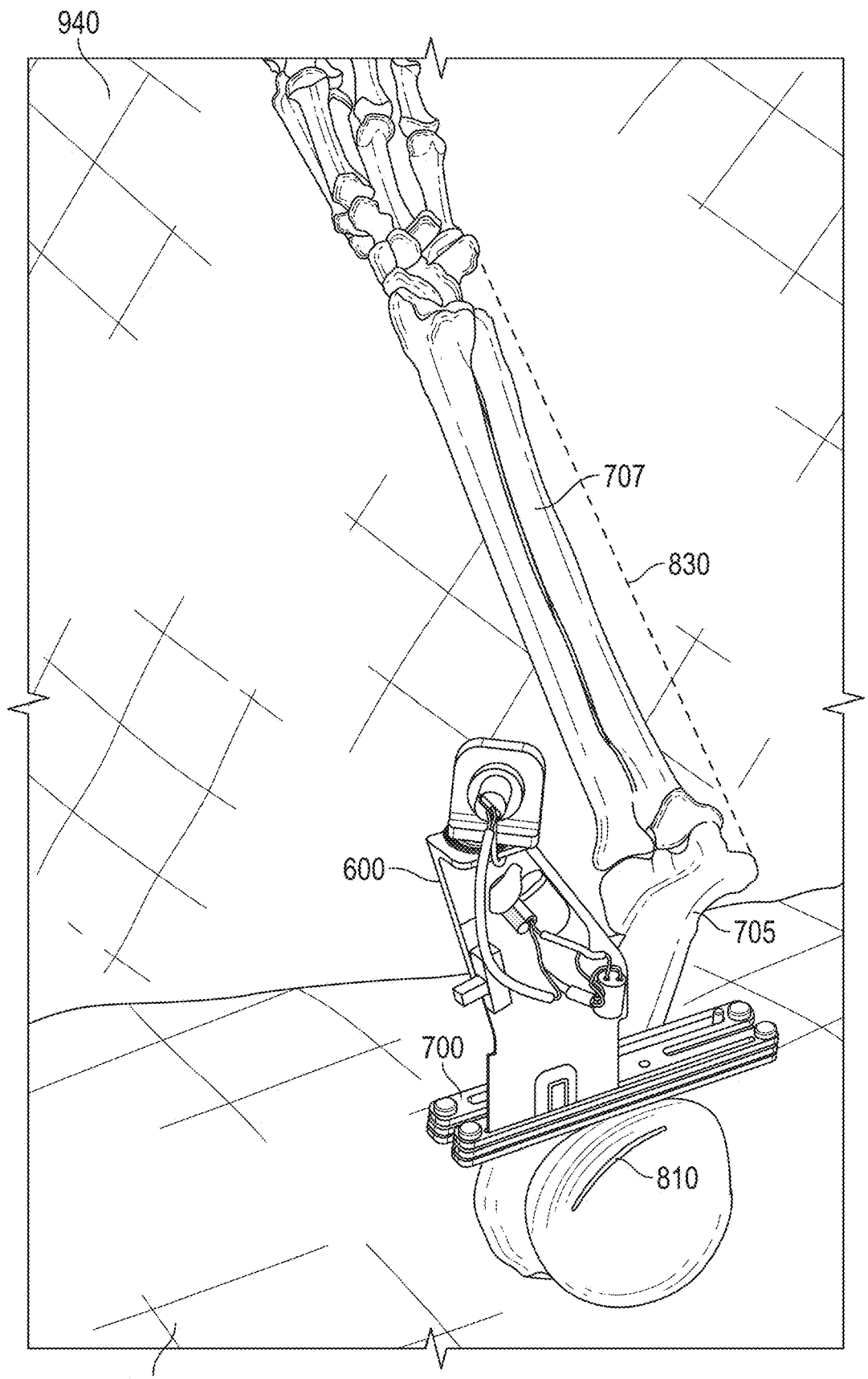
FIG. 9 depicts a top view of an alternate embodiment of a laser guide inserted into a surgical block with laser lines emitting from said alternate embodiment.

FIGS. 8 and 9 depict views of adjustable laser guide 600 inserted into top slit 710 of surgical block 700 affixed to humerus bone 705. The humerus bone 705 is connected to the forearm bones 707. Also depicted are first laser projection 810 and second laser projection 820. First laser projection 810 is from light emitted from horizontal lasers 130 of adjustable laser guide 600 (thus, FIGS. 8 and 9 show light from both horizontal lasers 130 emitting light in the same plane and projecting the same line), and second laser projection 820 is from light emitted from vertical laser 140 of adjustable laser guide 600. Second laser projection 820 is further comprised of first segment 825 and second segment 827 (first segment 825 is not shown in FIG. 9). As depicted, adjustable laser guide is configured (by adjustment of one or both of rotation of vertical laser 140 relative to end plate 180 and rotation of end plate 180 relative to base plate 110). As shown, first laser projection 810 is along a top of humerus bone 705, depicting the location where a cut will be made into humerus bone 705 through surgical block 700. First segment 825 of second laser projection 820 is on first surface 840 parallel to humerus bone 705 and second segment 827 of second laser projection 820 is on second surface 850, parallel to forearm bones 707.

It is a goal of adjustable laser guide 600 to allow a surgeon to confirm and align the location of cut into bone (as shown, in a shoulder replacement surgery). First laser projection 810 provides a visual indication of the location of a cut, and second laser projection provides a visual indication of the angle of the cut relative to the longitudinal axis of humerus bone 705. Embodiments of laser guide 100, surgical block 200, and laser guided surgical method 400 and/or components of any thereof, can be implemented in any combination of components as understood by one skilled in the art. Further, it will be obvious to those having skill in the art that many changes may be made to the details of the above-described embodiments without departing from the underlying principles of the invention. For example, any suitable combination of the components of laser guide 100, surgical block 200, and laser guided surgical method 400 is possible.

The foregoing description of the embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the allowed claims and their equivalents. The scope of the present invention should, therefore, be determined only by the following allowed claims.

What is claimed is:

1. A laser guide comprising: a base plate, an end plate, a horizontal laser assembly, a vertical laser assembly, a switch, and a battery; wherein said horizontal laser assembly and said vertical laser assembly both comprise a laser emitting device and a lens, said lens being affixed to a light emitting end of said laser emitting device;
   wherein said horizontal laser assembly is affixed to said base plate, parallel to said base plate, and said vertical laser assembly is affixed to said end plate, orthogonal to said end plate;
   wherein said switch and said battery are affixed to said base plate, and said switch, said horizontal laser assembly and said vertical laser assembly are electrically connected to said battery; and
   wherein said end plate is rotationally connected to said base plate.

2. The laser guide of claim 1, wherein said base plate further comprises an insertion plate and said insertion plate further comprises a raised flexible tab; wherein said insertion plate is on an opposite side of said base plate from said end plate; and wherein said insertion plate may be inserted into a surgical block and held in place by said raised flexible tab.

3. The laser guide of claim 2, wherein said base plate and said insertion plate are coplanar, said base plate extends beyond a width of said insertion plate, and said end plate is offset horizontally from said insertion plate.

4. The laser guide of claim 3, wherein said lens of said horizontal laser assembly refracts laser light into a horizontal plane and said lens of said vertical laser assembly refracts laser light into a vertical plane.

5. The laser guide of claim 4, wherein said surgical block is configured to be mounted on a human bone for performing a surgery, when said laser guide is inserted into said surgical block, and said surgical block is mounted on said human bone for performing said bone surgery, and said laser guide is switched on, then said horizontal laser assembly refracts laser light onto said human bone creating a horizontal projection, and said horizontal projection is a proposed location for performing a cut of said bone surgery in said horizontal plane.

6. The laser guide of claim 5, wherein when said laser guide is inserted into said surgical block, said vertical laser assembly refracts laser light onto bone below said human bone creating a vertical projection, and said vertical projection indicates alignment of said cut of said bone surgery.

7. The laser guide of claim 6, wherein said end plate and said base plate are rotationally connected by a rotational locking mechanism, allowing said end plate and said base plate to be fixed in a coplanar position when locked and also allowing said base plate to rotate at least 180 degrees to allow projection of laser light in an opposite direction and allowing said laser guide to be used with one or more types of human bones.

8. The laser guide of claim 7, wherein said rotational locking mechanism allows said base plate to be rotationally locked in place at 0 degrees, 45 degrees, 135 degrees, 180 degrees, 225 degrees, and 315 degrees relative to said base plate.

9. The laser guide of claim 7, wherein said rotational locking mechanism comprises a first ridged connector plate having first ridges and a second ridged connector plate having second ridges, wherein compressive force holds said first ridges against said second ridges and said first ridged connector plate is rotatable relative to said second ridged connector plate upon application of rotational force sufficient to overcome said compressive force.

10. The laser guide of claim 9, wherein said laser guide further comprises a second horizontal laser assembly comprising a laser emitting device and a lens, said lens being affixed to a light emitting end of said laser emitting device; wherein said second horizontal laser assembly is affixed to said base plate parallel to said base plate; and wherein said second horizontal laser assembly refracts laser light into said horizontal plane.

11. The laser guide of claim 10 wherein said vertical laser assembly is rotatable relative to said end plate in an axis orthogonal to said end plate.

* * * * *